(12) United States Patent
Oba et al.

(10) Patent No.: US 9,675,549 B2
(45) Date of Patent: Jun. 13, 2017

(54) TABLET CONTAINING COMPOSITE WITH CYCLODEXTRIN

(71) Applicant: AMBIT BIOSCIENCES CORPORATION, San Diego, CA (US)

(72) Inventors: Shinsuke Oba, Chuo-ku Tokyo (JP); Hiroyasu Toyota, Chuo-ku Tokyo (JP); Satomi Ikeuchi, Tokyo (JP); Takumi Hara, Tokyo (JP); Emiko Murayama, Tokyo (JP); Kei Motonaga, Tokyo (JP)

(73) Assignee: Ambit Biosciences Corporation, San Diego, CA (US)

( * ) Notice: Subject to any disclaimer, the term of this patent is extended or adjusted under 35 U.S.C. 154(b) by 0 days.

(21) Appl. No.: 14/432,387

(22) PCT Filed: Sep. 30, 2013

(86) PCT No.: PCT/US2013/062577
§ 371 (c)(1),
(2) Date: Mar. 30, 2015

(87) PCT Pub. No.: WO2014/055397
PCT Pub. Date: Apr. 10, 2014

(65) Prior Publication Data
US 2015/0250720 A1    Sep. 10, 2015

(30) Foreign Application Priority Data

Oct. 1, 2012 (JP) ................................ 2012-219334

(51) Int. Cl.
| | | |
|---|---|---|
| A61K 9/00 | (2006.01) |
| A61K 47/12 | (2006.01) |
| A61K 47/38 | (2006.01) |
| A61K 47/14 | (2017.01) |
| A61K 47/26 | (2006.01) |
| A61K 47/40 | (2006.01) |
| A61K 31/5377 | (2006.01) |
| A61K 47/02 | (2006.01) |
| A61K 9/20 | (2006.01) |
| A61K 9/46 | (2006.01) |

(52) U.S. Cl.
CPC .......... *A61K 9/0056* (2013.01); *A61K 9/0007* (2013.01); *A61K 9/0053* (2013.01); *A61K 9/0095* (2013.01); *A61K 9/205* (2013.01); *A61K 31/5377* (2013.01); *A61K 47/02* (2013.01); *A61K 47/12* (2013.01); *A61K 47/14* (2013.01); *A61K 47/26* (2013.01); *A61K 47/38* (2013.01); *A61K 47/40* (2013.01)

(58) Field of Classification Search
None
See application file for complete search history.

(56) References Cited

U.S. PATENT DOCUMENTS

| | | | | |
|---|---|---|---|---|
| 7,820,657 B2 * | 10/2010 | Bhagwat | ............ | C07D 513/04 514/233.2 |
| 7,968,543 B2 * | 6/2011 | James | ................ | A61K 31/5377 514/231.5 |
| 8,357,690 B2 | 1/2013 | Armstrong et al. | | |
| 8,551,963 B2 | 10/2013 | Apuy et al. | | |
| 8,865,710 B2 | 10/2014 | Corringham et al. | | |
| 8,883,783 B2 | 11/2014 | Bhagwat et al. | | |
| 2006/0135621 A1 * | 6/2006 | Neckebrock | .......... | C07C 315/04 514/619 |
| 2009/0131426 A1 * | 5/2009 | Bhagwat | ............ | C07D 513/04 514/233.2 |
| 2010/0292177 A1 * | 11/2010 | Armstrong | ............ | A61K 9/0019 514/27 |
| 2012/0070410 A1 * | 3/2012 | Apuy | ................... | C07D 513/04 424/85.4 |
| 2012/0129850 A1 * | 5/2012 | Bhagwat | ............ | C07D 513/04 514/233.2 |
| 2012/0258081 A1 * | 10/2012 | Corringham | ......... | A61K 31/429 424/93.7 |

FOREIGN PATENT DOCUMENTS

| | | |
|---|---|---|
| EP | 1 295 595 A1 | 3/2003 |
| JP | S60-161925 A | 8/1985 |
| JP | 2003-313145 A | 11/2003 |
| JP | 2005-314413 A | 11/2005 |
| WO | 02/02083 A1 | 1/2002 |
| WO | 2010/132787 A1 | 11/2010 |

OTHER PUBLICATIONS

Fragrance Journal, 1985, No. 75, p. 83-86.
Handbook of Pharmaceutical Excipients, Yakuji Nippo Limited, 2007, 5th edition, p. 762.

* cited by examiner

*Primary Examiner* — Richard Schnizer
*Assistant Examiner* — Katherine Peebles
(74) *Attorney, Agent, or Firm* — Jones Day (57) ABSTRACT

Provided herein is a tablet comprising, as a drug, N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof, which is a medicament for treating acute myeloid leukemia (AML), the tablet characterized by comprising a composite of N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof and hydroxypropyl-β-cyclodextrin in a ratio ranging from 1:8 to 1:20.

9 Claims, 2 Drawing Sheets

TABLET CONTAINING COMPOSITE WITH CYCLODEXTRIN

CROSS REFERENCE TO RELATED APPLICATION

This application is a National stage under 35 U.S.C. 371(c) of International Application No. PCT/US2013/062577, filed Sep. 30, 2013, which claims the benefit of the priority of Japanese Provisional Application No. JP 2012-219334, filed Oct. 1, 2012, the disclosure of each of which is incorporated herein by reference in its entirety.

FIELD

Provided herein is a tablet composition comprising N-(5-tert-butyl-isoxazol-3-yl)-N'-{4-[7-(2-morpholin-4-yl-ethoxy)imidazo[2,1-b][1,3]benzothiazol-2-yl]phenyl}urea (hereinafter sometimes referred to as "AC220") or a pharmaceutically acceptable salt thereof. The tablet composition has rapid dispersibility and dissolution and high bioavailability. In certain embodiments, the tablet is used as a medicament for treating acute myeloid leukemia (AML). More particularly, provided herein is a tablet comprising a composite of AC220 or a pharmaceutically acceptable salt thereof and hydroxypropyl-β-cyclodextrin (hereinafter sometimes referred to as "HPBCD").

BACKGROUND ART

It has been reported that N-(5-tert-butyl-isoxazol-3-yl)-N'-{4-[7-(2-morpholin-4-yl-ethoxy)imidazo[2,1-b][1,3]benzothiazol-2-yl]phenyl}urea (AC220) or a pharmaceutically acceptable salt thereof is effective in treating proliferative diseases in which FMS-Like Tyrosine Kinase-3 (FLT3) is involved, such as leukemia in one embodiment, and such as AML in another embodiment. See International Publication Nos. WO 2010/132787, WO 2007/109120, and WO 2009/038757.

AC220 dihydrochloride (2HCl) is currently being developed for treatment of AML. This compound has molecular weight of 663.6 and the following formula:

•2HCl

International Publication No. WO 2010/132787 discloses a spray-dried powder or a lyophilized powder of AC220 in combination with cyclodextrins (as a carrier), which is disclosed as an anti-gelling agent. In certain embodiments, the spray-dried powder or lyophilized powder comprises AC220.2HCl and HPBCD in a ratio of 1:5 to 1:20 by weight. It is further described in WO 2010/132787 that in certain embodiments, the spray-dried powder is dissolved (reconstituted) before use and administered in a liquid dosage form. WO 2010/132787 also discloses a formulation comprising a spray-dried powder of AC220.2HCl and HPBCD at a 1:10 ratio by weight, which is dissolved before use and administered orally in a liquid dosage form (hereinafter this liquid dosage form is sometimes referred to as "AC220 solution (1:10)"), see Examples 6 to 8. WO 2010/132787 further discloses solid preparations of AC220 for oral administration, for example, liquid capsules using AC220 and GELUCIRE™ 44/14 (lauroyl polyoxylglycerides), and capsules comprising AC220 and HPBCD in a ratio of 1:2 by weight in combination with mannitol and EXPLOTAB™ (sodium starch glycolate).

However, no tablets having bioavailability equivalent to that of the preparation that is dissolved before use comprising the spray-dried material of AC220.2HCl and HPBCD at a 1:10 ratio by weight (administered in a liquid dosage form: AC220 solution (1:10)) disclosed in WO 2010/132787 have been reported until now. Development of tablets which are excellent in dispersibility, dissolution, and stability and which can achieve the bioavailability equivalent to that of the preparation that is dissolved before use disclosed in WO 2010/132787, is desired.

SUMMARY

Provided herein is a tablet composition which includes AC220 or a pharmaceutically acceptable salt thereof as an active ingredient, and which has improved dispersibility, dissolution, and bioavailability equivalent to that of the preparation that is dissolved before use comprising the spray-dried material of AC220.2HCl and HPBCD at a 1:10 ratio by weight (administered in a liquid dosage form: AC220 solution (1:10)) disclosed in WO 2010/132787, and which are very convenient to use.

To produce a tablet of AC220 having bioavailability equivalent to that of the AC220 preparation that is dissolved before use (administered in a liquid dosage form: AC220 solution (1:10)) disclosed in WO 2010/132787, the present inventors prepared tablets of AC220 using various carriers for medicinal preparation, but could not obtain tablets having sufficient dispersibility and dissolution.

Under these circumstances, the properties of AC220 were examined, particularly, molecular state in an aqueous solution, and it was observed that AC220 had strong intermolecular interactions due to aggregate formation via π-π stacking and due to network formation by hydrogen bonding, and that these intermolecular interactions resulted in gelation of the aqueous solution of AC220 and interfered with dispersion of AC220 from tablets. It was further observed that the intermolecular interactions are likely suppressed when AC220 forms a composite with HPBCD in a ratio ranging from 1:8 to 1:20 by weight.

Therefore, tablets were prepared which had suppressed the intermolecular interactions of AC220 by using a composite of AC220 and HPBCD. However, unexpectedly, tablets using general formulations comprising the composite of AC220 and HPBCD did not show sufficient dispersibility and dissolution.

The tablets comprising the composite of AC220 and HPBCD exhibited the following characteristics:

(1) certain excipients in disintegrators, lubricants, and the like inhibited the disintegration and the dissolution of the tablets comprising the composite of AC220 and HPBCD, and the disintegration and the dissolution were improved by limiting the amounts of the excipients, and (2) since the composite of AC220 and HPBCD per se exhibited unexpectedly excellent moldability and ease of disintegration, a tablet having excellent moldability and ease of disintegration, and also excellent stability, could be obtained even when the amounts of commonly used excipients such as disintegrators and lubricants were limited.

In certain embodiments, provided herein is a tablet comprising, as an active ingredient, AC220 or a pharmaceutically acceptable salt thereof, wherein AC220 or a pharmaceutically acceptable salt thereof forms a composite with hydroxypropyl-β-cyclodextrin in a ratio ranging from 1:8 to 1:20 by weight.

In certain embodiments, the tablet has a dissolution rate (D30 min) of about 85% or more after 30 minutes from the beginning of a dissolution test of the United States Pharmacopeia USP 34-NF 29 (paddle method, 50 rpm, 0.1 N hydrochloric acid, 900 mL).

In certain embodiments, the tablet comprises the composite in an amount of about 50% by weight or more of the total weight of the preparation.

In certain embodiments, the tablet comprises the composite in an amount of about 80% by weight or more of the total weight of the preparation.

In certain embodiments, the tablet comprises the composite in an amount of about 85% by weight or more of the total weight of the preparation.

In certain embodiments, the tablet comprises a disintegrator in an amount of about 10% by weight or less of the total weight of the preparation, and a lubricant in an amount of about 2.5% by weight or less of the total weight of the preparation.

In certain embodiments, the tablet comprises the total amount of an excipient selected from the group consisting of a binder, a diluent, a lubricant, a glidant, a pH adjustor, a foaming agent, a sweetener, a flavor, a coloring agent, and a stabilizer in about 0 to 50% by weight with respect to the total weight of the preparation.

In certain embodiments, the tablet comprises a foaming agent comprising a carbonate and a solid acid in an amount of about 10 to 45% by weight of the total weight of the preparation, a diluent in an amount of about 0 to 20% by weight of the total weight of the preparation, and a lubricant in an amount of about 0 to 2.5% by weight or less of the total weight of the preparation.

In certain embodiments, the tablet comprises a lubricant in an amount of about 0.5 to 2.5% by weight of the total weight of the preparation, a diluent in an amount of about 0 to 10% by weight of the total weight of the preparation, and a binder in an amount of about 0 to 5% by weight of the total weight of the preparation.

In certain embodiments, the tablet comprises a disintegrator in an amount of about 0 to 3% by weight of the total weight of the preparation.

In certain embodiments, the tablet comprises a lubricant in an amount of about 0.5 to 2.5% by weight of the total weight of the preparation, a diluent in an amount of about 0 to 10% by weight of the total weight of the preparation, and a binder in an amount of about 0 to 5% by weight of the total weight of the preparation.

In certain embodiments, the tablet comprises (1) a lubricant selected from the group consisting of calcium stearate and magnesium stearate in an amount of about 0.5 to 1.5% by weight of the total weight of the preparation, or a lubricant selected from the group consisting of talc and sodium stearyl fumarate in an amount of about 0.5 to 2.5% by weight of the total weight of the preparation, (2) a diluent selected from the group consisting of microcrystalline cellulose and D-mannitol in an amount of about 3 to 10% by weight of the total weight of the preparation, and (3) hydroxypropyl cellulose in an amount of about 0 to 4% by weight of the total weight of the preparation.

In certain embodiments, the tablet comprises (1) magnesium stearate in an amount of about 1% by weight of the total weight of the preparation, (2) a diluent selected from the group consisting of microcrystalline cellulose and D-mannitol in an amount of about 4 to 7.5% by weight of the total weight of the preparation, and (3) hydroxypropyl cellulose in an amount of about 0 to 4% by weight of the total weight of the preparation.

In certain embodiments, the tablet is obtainable by forming a composition comprising the composite into a tablet.

In certain embodiments, the tablet is a coated tablet.

In certain embodiments, the coating is a film coating.

In certain embodiments, the tablet comprises a composite of AC220 or a pharmaceutically acceptable salt thereof and hydroxypropyl-β-cyclodextrin in a ratio of 1:10 by weight.

In certain embodiments, the composite is a spray-dried powder.

In certain embodiments, the composite is a lyophilized powder.

In certain embodiments, the tablet comprises AC220 dihydrochloride.

In the preset specification, a composite of N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof and hydroxypropyl-β-cyclodextrin is sometimes referred to as "composite of AC220 and HPBCD". Moreover, the composite specified by ratio, for example the composite in a ratio ranging from 1:8 to 1:20 by weight is sometimes referred to as "composite of AC220 and HPBCD in a ratio of 1:8 to 1:20 by weight".

In certain embodiments, the tablets provided herein are free from the intermolecular interactions of AC220, in which the preparation can be disintegrated and dispersed rapidly, and have bioavailability equivalent to that of the preparation that is dissolved before use comprising the spray-dried material of AC220.2HCl and HPBCD at a 1:10 ratio by weight (administered in a liquid dosage form: AC220 solution (1:10)) disclosed in WO 2010/132787, and which preparation can be easily produced and is convenient to use.

DESCRIPTION OF EMBODIMENTS

Hereinafter, various embodiments of the tablets provided herein will be explained.

AC220 or a pharmaceutically acceptable salt thereof which is disclosed herein has the chemical name: N-(5-tert-butyl-isoxazol-3-yl)-N'-{4-[7-(2-morpholin-4-yl-ethoxy) imidazo[2,1-b][1,3]benzothiazol-2-yl]phenyl}urea, or a pharmaceutically acceptable salt thereof, which is disclosed in WO2007/109120 and WO2009/038757. The drug may be one of various salts, hydrates, solvates, and crystalline forms of AC220 disclosed in these publications. The drug is a hydrochloride salt of AC220 in one embodiment, and AC220.2HCl in another embodiment.

The amount of AC220 or a pharmaceutically acceptable salt thereof is not limited, so long as it is a therapeutically or prophylactically effective amount, for example, from about 12 mg to about 450 mg per day in one embodiment, from about 12 mg to about 145 mg in another embodiment, from about 30 mg to about 135 mg in still another embodiment, 30 mg, 40 mg, 45 mg, 50 mg, 60 mg, 70 mg, 80 mg, 90 mg, 120 mg, and 135 mg in still another embodiment, 60 mg in still another embodiment, and 90 mg in still another embodiment. The daily dose may be divided into multiple doses administered several times a day, if necessary. The above-mentioned amount is the amount of AC220 in one embodiment, and the amount of AC220.2HCl in another embodiment.

It was confirmed that aggregate formation via π-π stacking between aromatic rings and network formation by intermolecular hydrogen bonding are involved, as intermolecular interactions, in gel formation of an aqueous solution of AC220, as shown in Example 1 described below.

In this regard, WO 2010/132787 does not disclose the intermolecular interaction of AC220, but discloses that HPBCD was added to AC220 as an anti-gelling agent in a ratio (AC220:HPBCD) of 1:10 by weight, and the mixture was spray-dried to prepare a preparation that is dissolved before use, then the preparation was reconstituted by aqueous solution to obtain a liquid dosage form in which gelling was prevented (for example, paragraphs [0073] to [0075] and [0088], and Examples 6 to 8). It is suggested that the gelling in aqueous liquid dosage form was prevented as a result of suppression of the intermolecular interaction of AC220 on the basis of the examination of the intermolecular interaction of AC220. That is to say, the composite of AC220 and HPBCD in a ratio of about 1:10 by weight is believed to effectively suppress the intermolecular interaction of AC220.

The composite of AC220 and HPBCD in the present disclosure is found in a ratio of AC220 or a pharmaceutically acceptable salt thereof and HPBCD by weight ranging from 1:8 to 1:20 in one embodiment, 1:10 to 1:15 in another embodiment, and 1:10 in still another embodiment. The composite of AC220 and HPBCD is granulated or powdered solid of mixture of AC220 and HPBCD, which is suitable for tableting and prepared by a conventional methods. The composite of AC220 and HPBCD is a spray-dried powder or a lyophilized powder in one embodiment, a spray-dried powder in another embodiment, and lyophilized powder in still another embodiment.

In the case that the amount of HPBCD to AC220 is less than the above amount, there is a possibility that the intermolecular interaction of AC220 in the preparation is not completely suppressed, and the dispersion and the dissolution of such a tablet will be delayed or reduced, depending on the water content or pH in the digestive tract of a patient.

i) Composite

In certain embodiments, the composite in the tablets provided herein is prepared by conventional methods. In certain embodiments, AC220 or a pharmaceutically acceptable salt thereof and HPBCD are dissolved in an inert solvent and stirred to obtain a mixture. In certain embodiments, the mixture is dried lyophilized or spray-dried to prepare the composite. In certain embodiments, the methods include disintegration and/or particle size regulation steps. In certain embodiments, 1 part by weight of AC220.2HCl and 8 to 20 parts by weight of HPBCD are dissolved in an inert solvent such as water and the mixture is spray-dried to obtain a powdered composite.

The spray-dried powders obtained using 10 parts by weight of HPBCD with 1 part by weight of AC220.2HCl are disclosed in Examples 6 to 8 of WO 2010/132787. These powders are disclosed as compositions for a preparation that is dissolved before use, which is dissolved in aqueous solution and administered in a liquid dosage form, and in certain embodiments, is used as the composite in the present disclosure for the production of the tablet provided herein.

In the present specification, a spray-dried powder of AC220.2HCl and HPBCD at a ratio of 1:10 by weight obtained by a similar method as disclosed in Examples 6 to 8 of WO 2010/132787 is sometimes referred to as "AC220-HPBCD (1:10)" hereinafter.

The amount of the composite of AC220 and HPBCD in the tablets provided herein is such that the tablet disintegrates rapidly, and a rapid dissolution is achieved. In one embodiment, the amount of the composite with respect to the total weight of the tablet is, 50% by weight or more, in another embodiment, 60% by weight or more, in another embodiment, 70% by weight or more, in still another embodiment, 80% by weight or more, in still another embodiment, 85% by weight or more, and in still another embodiment, and 88% by weight or more.

In certain embodiments, the tablets are coated tablets, and the amount of composite with respect to the total weight of uncoated tablets is 80% by weight or more, in one embodiment, 85% by weight or more, and in another embodiment, 90% by weight or more. In certain embodiments, the tablets contain a foaming agent (effervescent tablets) comprising a pharmaceutically acceptable solid acid and a compound comprising a carbonate and/or a hydrogen carbonate in an amount of about 10 to 45% by weight. In certain embodiments, effervescent tablets contain the composite in an amount of about 50% by weight or more, in one embodiment, 55% by weight or more, and in another embodiment, 60% by weight or more.

ii) Excipients

It was observed that when the composite of AC220 and HPBCD was used to prepare a tablet by conventional methods using excipients commonly used in the pharmaceutical field, release and dissolution were unexpectedly delayed. Therefore, in one embodiment, in the tablet provided herein, the types of excipients and the amounts of excipients are appropriately selected in accordance with various conditions, for example, the type of excipient (properties such as molecular weight, solubility, and viscosity), the types and amounts of other excipients, the type and amount of composite, and its dosage form and the formulation step (granulation method and tabletting method).

a) Disintegrators

Disintegrators are excipients to improve the disintegration of a preparation, more particularly, they are excipients to be added to disintegrate a tablet by absorbing water in the body after administration, swelling, and thereby facilitating release of the active ingredient. However, as described in Reference Example 3 in this specification, when general-purpose disintegrators which absorb water and swell were added to tablets containing the AC220-HPBCD (1:10), no disintegration due to the swelling of the tablets was confirmed. In certain embodiments, the disintegration and the dissolution of the tablets were reduced because of certain disintegrators.

In certain embodiments, the amount of disintegrators in the tablets provided herein is limited to a range in which the disintegration and the dissolution of the tablet are not reduced. In certain embodiments, the tablets do not contain any disintegrators that do not improve the disintegration.

The amount of disintegrator in the tablets is selected such that the disintegration and dissolution of the tablet are not reduced. The amount of disintegrator in the tablet varies based on, for example, the types and properties of disintegrators, the types and amounts of other excipients, the type and amount of the composite, and their dosage forms and the formulation step (granulation method and tabletting method). In certain embodiments, the amount of disintegrator in the tablet is about 10% by weight or less based on the total weight of the tablet, in one embodiment, 5% by weight or less, and in another embodiment, and 3% by weight or less. In one embodiment, the tablet provided herein does not contain any disintegrators.

The disintegrators in the present disclosure are excipients which are expected to exhibit an effect of disintegrating tablets by absorbing water in the digestive tract and swelling. Examples of the disintegrators include:

Low-substituted hydroxypropyl cellulose (L-HPC) (product name: LH-11, LH-21, LH-22, LH-31, and the like)

Crospovidone (product name: Kollidon CL, Polyplasdone XL, Crospovidone, and the like)

Croscarmellose sodium (product name: Kicolate, Ac-Di-Sol, Primellose, and the like)

Sodium starch glycolate (product name: Primojel, GLYCOLYS, EXPLOTAB, and the like)

Sodium alginate

Carmellose, carmellose calcium, and carmellose sodium

Glycerin fatty acid ester

Low-substituted sodium carboxymethyl starch

Partially pregelatinized starch (product name: LYCATAB C, PCS, Graflow, starch 1500, and the like).

(b) Binders

Binders are classified as excipients which impart the stickiness for maintaining quality after tabletting. It was found that binders having a high molecular weight and binders having a high viscosity at the time of dissolution reduced the initial dissolution of the tablet provided herein. The amount of a binder in the tablets provided herein varies based on, for example, the type of binders (properties such as molecular weight, solubility, and viscosity), the type and amount of other excipients, the type and amount of the composite, and its dosage form and the formulation step (granulation method and tabletting method). In certain embodiments, the amount of the binder is about 10% by weight or less of the total weight of the preparation, in one embodiment, the binder is about 5% by weight or less, in another embodiment, the binder is about 3% by weight or less. In one embodiment, the binder is about 3% by weight. In one embodiment, the binder is about 1% by weight. In one embodiment, the tablet provided herein does not contain any binder. In certain embodiments, a binder having a low molecular weight and a low viscosity, such as HPC-SSL-SFG, only weakly inhibits the release, and thus, the influence of the addition of the binder on the dissolution is small. By contrast, in certain embodiments, a binder having a high viscosity such as HPC-L strongly inhibits the release, and thus, it is preferable to add such binder in smaller amounts.

Examples of binders useful in the tablets provided herein include:

Hydroxypropyl cellulose (product name: HPC-SSL, HPC-SL, HPC-L, METOLOSE SR, KLUCEL-EF, KLUCEL-LF, KLUCEL-JF, and the like)

Hypromellose (product name: TC-5E, TC-5R, TC-5M, TC-5S, METOLOSE 65SH, METHOCEL F, and the like)

Methyl cellulose (product name: METOLOSE SM, METHOCEL A, and the like)

Hydroxyethyl cellulose

Hydroxyethyl methylcellulose

Hydroxypropyl starch

Povidone (product name: Kollidon, Plasdone, and the like)

Corn starch

Potato starch

Rice starch

Gelatin (c) Lubricants

Examples of lubricants include magnesium stearate, calcium stearate, sucrose fatty acid ester, polyethylene glycol, talc, sodium stearyl fumarate, and stearic acid. Lubricants are hydrophobic, and the amount of lubricants in tablets is limited, depending on the degree of hydrophobicity of each lubricant. When a lubricant(s) is used in the tablet provided herein, in certain embodiments, about 0 to 2.5% by weight of lubricant(s) is added with respect to the total weight of the tablet. In another embodiment, (1) about 0.5 to 1.5% by weight of a lubricant(s) selected from the group consisting of magnesium stearate and calcium stearate with respect to the total weight of the tablet, or (2) about 0.5 to 2.5% by weight of a lubricant(s) selected from the group consisting of sodium stearyl fumarate and talc, is added. In still another embodiment, about 1% of by weight, with respect to the total weight of the preparation, of magnesium stearate is added.

(d) Diluents

Diluents are excipients which are used for diluting formulation components such as active ingredients and adjusting them to amounts appropriate to the formulation, and in some cases, for imparting stability, improved moldability, and the like. Diluents are also referred to as fillers or bulking agents. Examples of diluents include lactose, glucose, sucrose, maltose (preferably candy powder (containing 83% or more of maltose)), trehalose, sugars such as lactose and fructose, sugar alcohols such as mannitol, xylitol, maltitol, sorbitol, and erythritol, and crystalline cellulose. In one embodiment, the diluent used in the tablets provided herein is D-mannitol such as granulated mannitol (product name: Parteck M100, M200, Pearlitol 100SD, 200SD, and the like) or crystalline cellulose (product name: Ceolus PH-101, PH-102, PH-301, PH-302, UF-711, UF-702, and the like). Another embodiment, the diluent is crystalline cellulose. Still another embodiment, the diluents is crystalline cellulose (product name: Ceolus PH-102).

(e) Other Excipients

The tablet provided herein may contain various excipients other than the above-mentioned excipients, which are pharmaceutically acceptable and used as excipients. Examples of the other excipients include, but are not limited to, glidants, pH adjustors, foaming agents, sweeteners, flavors, coloring agents, stabilizers, and solubilizing agents.

The amount of these excipients in the tablets provided herein is selected such that the dissolution of AC220 from the tablet is not negatively affected. In one embodiment, the total amount of these excipients is about 40% by weight or less of the total weight of the tablet, in one embodiment, the amount is 30% by weight or less, in another embodiment, the amount is 20% by weight or less. In certain embodiments, it was observed that the hydrophobic excipients inhibited the penetration of water into the tablet. In certain embodiments, the total amount of hydrophobic excipients in the total excipients is about 5% by weight or less of the total weight of the tablet. In one embodiment, the total amount of hydrophobic excipients in the total excipients is about 2% by weight or less, in another embodiment, about 1.5% by weight or less, and in still another embodiment, about 1% by weight or less.

In certain embodiments, the tablets comprise a glidant selected from silicon dioxide, light anhydrous silicic acid, titanium oxide, stearic acid, and talc.

In certain embodiments, the tablets comprise a pH adjustor selected from acidic substances, such as citric acid, tartaric acid, and malic acid. Since AC220 exhibits a high solubility at low pH, the addition of acidic substances is expected to improve the solubility of AC220 in the lower digestive tract from the small intestine.

In certain embodiments, the tablets comprise a sweetener selected from sodium saccharin, aspartame, stevia, and thaumatin.

In certain embodiments, the tablets comprise a flavors selected from lemon, lemon lime, orange, and menthol.

In certain embodiments, the tablets comprise a coloring agent selected from edible pigments such as food yellow No. 5, food red No. 2, and food blue No. 2, edible lake pigments, and colcothar.

In certain embodiments, the tablets comprise a stabilizer, i.e., a substance capable of stabilizing AC220.

In certain embodiments, the tablets comprise a solubilizing agent selected from the above-mentioned acidic substances.

In certain embodiments, the tablet provided herein is an effervescent tablet. In certain embodiments, the effervescent tablet provided herein is a tablet comprising a pharmaceutically acceptable foaming agent, in one embodiment, the tablet comprises an effervescent mixture comprising a solid acid and a compound comprising a carbonate and/or a hydrogen carbonate. In one embodiment, when the tablet is brought into contact with water, effervescence occurs and the tablet can be effectively dissolved. Examples of the solid acid include citric acid and tartaric acid. Examples of the compound comprising a carbonate and/or a hydrogen carbonate include calcium carbonate, sodium carbonate, and sodium bicarbonate.

The tablets provided herein contain a combination of two or more excipients.

The tablet provided herein is not limited, so long as it is a preparation which is defined as a general medicament.

In certain embodiment, the tablet provided herein is prepared by compression-molding the composite of AC220 and HPBCD (spray-dried powder in one embodiment, AC220-HPBCD(1:10) in another embodiment), together with an excipient(s) if necessary. Any conventional method for obtaining a tablet can be used, for example, the methods described in pharmacopoeias such as the Japanese Pharmacopoeia, the U.S. Pharmacopeia, and the European Pharmacopoeia, may be used. The exemplary methods include: (1) a method of directly tabletting the composite of AC220 and HPBCD (spray-dried powder in one embodiment, AC220-HPBCD(1:10) in another embodiment), together with an excipient(s) if necessary, and (2) a method of performing a wet granulation of the composite of AC220 and HPBCD (together with an excipient(s) if necessary) using a granulation liquid such as ethanol, acetone, or water to form granules, or performing a dry granulation of the composite of AC220 and HPBCD (together with an excipient(s) if necessary) to form granules, and compression-molding the resulting granules (after mixing the other component(s) with the granules if necessary).

In the compression-molding (tabletting), the mixture is tabletted using a rotary tabletting machine to obtain tabletted products. Examples of the apparatus for tabletting include: a rotary tabletting machine, a single punch tabletting machine, and an oil press.

Any tabletting conditions suitable for tablet molding can be used. In certain embodiments, tabletting pressure is used such that the tablets are not damaged during the manufacturing process. The tabletting pressure may be, for example, from about 2 kN to about 20 kN in one embodiment, and from about 5 kN to about 20 kN in another embodiment.

Any tablet hardness suitable for tablet molding can be used. The tablet hardness may be, for example, 80 N or more in one embodiment, and from 90 N to 200 N in another embodiment.

When the tablet is coated, conventional methods may be used for coating the tablet. Examples of the coating methods include pan coating and dip coating. Coating agents may be appropriately added alone or in a combination of two or more in appropriate quantities. The coating rate is not limited, so long as a film may be formed on the tablet. The coating rate is, for example, from 1% by weight to 5% by weight of the tablet weight. The coated tablet may be dried after the coating, and any pharmaceutically acceptable drying method may be used. Any pharmaceutically acceptable coating agent may be used. Examples of coating agents include product name: Opadry, Opadry II, and Opadry AMB.

The composite of AC220 and HPBCD, spray-dried powder in one embodiment, AC220-HPBCD(1:10) in another embodiment, exhibits excellent flow properties, and the tablet provided herein may be prepared by, optionally adding other excipients to the composite if necessary, and directly tabletting the composite or the resulting mixture. One embodiment of the tablet provided herein is a tablet prepared by directly tabletting the composite of AC220 and HPBCD or a mixture containing the composite of AC220 and HPBCD. Another embodiment of the tablet provided herein is a tablet prepared by directly tabletting the spray-dried powder or a mixture containing the spray-dried powder. In still another embodiment, the tablet provided herein is a tablet prepared by directly tabletting AC220-HPBCD(1:10) or a mixture containing the AC220-HPBCD(1:10). Still another embodiment is a film coated tablet of any of the above tablets prepared by direct tabletting.

The tablet provided herein exhibits rapid dispersion and dissolution. In one embodiment, the tablet provided herein has a dissolution rate (D30 min) of about 85% or more after 30 minutes from the beginning of a dissolution test of the United States Pharmacopeia USP 34-NF 29 (paddle method, 50 rpm, 0.1 N hydrochloric acid, 900 mL). In one embodiment, the dissolution rate (D30 min) is about 90% or more. In one embodiment, the dissolution rate (D30 min) is about 95% or more. In certain embodiments, the dissolution rate (D15 min) after 15 minutes from the beginning of the dissolution test is 60% or more, 70% or more, or 80% or more.

The tablet provided herein exhibits bioavailability equivalent to that of the preparation that is dissolved before use comprising the spray-dried material of AC220.2HCl and HPBCD at a 1:10 ratio by weight (administered in a liquid dosage form: AC220 solution (1:10)) disclosed in WO 2010/132787. For example, the $AUC_{0-24h}$ value of the tablet in the dog BA test described below is 0.8 to 1.2 times that of AC220 solution (1:10) in one embodiment, 0.9 to 1.1 times in another embodiment, and 0.95 to 1.05 times in still another embodiment.

The tablet provided herein has a good stability during storage. In one embodiment, dissolution of the tablet is not reduced for at least 4 months, at least 6 months, at least 8 months, at least 10 months, or at least 12 months, in conventional packaging such as a bottle with a desiccant and an aluminum pouch. Examples of the tablet provided herein having such a stability during storage include a tablet or a film coated tablet in which the composite of AC220 or its pharmaceutically acceptable salt and HPBCD (in a ratio ranging from 1:8 to 1:20 by weight) in an amount of about 85% by weight or more of the total weight of the preparation and: (1) a lubricant selected from the group consisting of calcium stearate and magnesium stearate in an amount of about 0.5 to 1.5% by weight of the total weight of the preparation, or a lubricant selected from the group consisting of talc and sodium stearyl fumarate in an amount of about 0.5 to 2.5% by weight of the total weight of the preparation, (2) a diluent selected from the group consisting of microcrystalline cellulose and D-mannitol in an amount of about 3 to 10% by weight of the total weight of the preparation, and (3) hydroxypropyl cellulose in an amount of about 0 to 4% by weight of the total weight of the preparation. Another embodiment is a tablet or its film coated tablet in which the composite of AC220 or its pharmaceutically acceptable salt and HPBCD (in a ratio of 1:10 by weight) in an amount of about 85% by weight or more of the total weight of the preparation and: (1) magnesium stearate in an amount of about 0.5 to 1.5% by weight of the total weight of the preparation, and (2) microcrystalline cellulose in an amount of about 3 to 10% by weight of the total weight of the preparation.

EXAMPLES

The embodiments described below are intended to be merely exemplary, and those skilled in the art will recognize, or will be able to ascertain using no more than routine experimentation, numerous equivalents of specific compounds, materials, and procedures. All such equivalents are considered to be within the scope of the claimed subject matter and are encompassed by the appended claims.

The following evaluation methods and preparation methods were used to prepare and test the tablets.

Dissolution Test 1

In the dissolution test of the United States Pharmacopeia USP 34-NF 29 (paddle method, 50 rpm, 0.1 N hydrochloric acid, 900 mL), a dissolution rate (D15 min) 15 minutes after the beginning of the test and/or a dissolution rate (D30 min) 30 minutes after the beginning of the test were measured.

Dissolution Test 2

A liquid-replacement dissolution test, in which a paddle method (50 rpm) was started using 300 mL of 0.03 N hydrochloric acid (pH 1.2), and the liquid conditions for the dissolution test were changed to pH 6.8 and 900 mL 30 minutes after the beginning of the test, was performed with reference to the dissolution test of the United States Pharmacopeia USP 34-NF 29, and dissolution rates were compared with that of the preparation that is dissolved before use comprising the spray-dried material of AC220.2HCl and HPBCD at a 1:10 ratio by weight (administered in a liquid dosage form: AC220 solution (1:10)) disclosed in WO 2010/132787. In the results of dissolution test 2, shown in Tables of the Reference Examples and the Examples as described below, the entry showing dissolution rate almost equivalent to or close to that of AC220 solution (1:10) is represented as "○", and t showing dissolution rate obviously lower than that of AC220 solution (1:10) is represented as "×".

The dissolution test of the preparation that is dissolved before use disclosed in WO 2010/132787 was performed using 9 mL (including 45 mg of AC220.2HCl) of a reconstituted liquid dosage form (AC220 solution (1:10)) prepared by reconstituting spray-dried powder of AC220.2HCl and HPBCD (in a ratio of 1:10 by weight) which was prepared by a similar method described in Examples 6 to 8 of WO 2010/132787, with water so as to give a concentration of 5 mg/mL.

Dog BA Test

The bioavailability of each preparation was evaluated using dogs. Preparations to be tested were administered to dogs which had been fasted overnight. In the case of the known AC220 preparation that is dissolved before use comprising the spray-dried material of AC220.2HCl and HPBCD at a 1:10 ratio by weight disclosed in WO 2010/132787, a reconstituted liquid dosage form (AC220 solution (1:10): 27 mL) containing 135 mg of the active ingredient was administered along with water (23 mL), and in the case of tablets, tablets (45 mg tablet×3 tablets) were administered along with water (50 mL). After the preparations were orally administered, blood was collected periodically over time. The drug concentration in plasma (ng/mL) was measured, and the maximum concentration in blood (Cmax: ng/mL) and the AUC from 0 to 24 hours ($AUC_{0-24h}$: ng*h/mL) were calculated. This test was performed using dogs the stomach conditions of which were acidic, assuming that the preparation will be administered to healthy people.

Direct Compression

A mixture of drug powder and excipients was compressed into tablets using an oil press. The drug powder and excipients were mixed in a mortar or a bag. In Tables of the Reference Examples and the Examples below, direct compression is represented as "DC".

Dry Granulation and Compression

A mixture of drug powder and desired excipients other than lubricants was compressed using an oil press, and pulverized using a mortar and a pestle or the like to obtain a granulated product. The resulting granulated product was mixed with a lubricant, and this mixture was compressed into tablets using an oil press with a tabletting pressure of 2 kN or 5 kN. In Tables of the Reference Examples and the Examples below, a method of obtaining tablets by the dry granulation and the compression using an oil press with a tabletting pressure of 2 kN or 5 kN is represented as "Granul.(2 kN)" or "Granul.(5 kN)", respectively.

Reference Example 1: Conventional Formulations

Commonly used excipients were used to obtain the tablets containing 45 mg of AC220.2HCl (45 mg tablets) with the formulations shown in Table 1. These tablets were evaluated by dissolution test 1. Further, tablets of Refs. 1c, 1d, and 1e were evaluated by dissolution test 2. The results are shown in Table 1.

TABLE 1

| Components (product name, code) | | Ref 1a | Ref 1b | Ref 1c | Ref 1d | Ref 1e |
|---|---|---|---|---|---|---|
| Drug | AC220-2HCl | 45 | 45 | 45 | 45 | 45 |
| Diluent | D-Mannitol | — | — | 221.4 | 161.9 | — |
| Diluent | Granulated mannitol (Pearlitol 200SD) | — | 206.1 | — | — | — |
| Diluent | Crystalline cellulose (Ceolus PH-102) | 206.1 | — | 36 | 36 | 43.2 |
| Disintegrator | Croscarmellose sodium (Kicolate) | — | — | 27 | 13.5 | — |
| Disintegrator | Sodium starch glycolate (Primojel) | 16.2 | 16.2 | — | — | — |
| Disintegrator | Crospovidone | — | — | 13.5 | — | — |
| Disintegrator | L-HPC (LH-21) | — | — | 13.5 | — | — |
| Foaming agent | Calcium carbonate | — | — | — | — | 60 |
| pH Adjustor/ Foaming agent | Tartaric acid | — | — | — | 100 | 30 |
| Lubricant | Magnesium stearate | 2.7 | 2.7 | 8 | 3.6 | 1.8 |
| Tablet (mg) | | 270 | 270 | 360 | 360 | 180 |
| Preparation method | | DC | DC | DC | DC | DC |
| Tablet size | | 9 mm, round | 9 mm, round | 10 mm, round | 10 mm, round | 8 mm, round |
| Dissolution test 1 (D30 min) | | <30% *1 | <10% *1 | 48% | 92% | 72% |
| Dissolution test 2 | | — | — | x | x | x |

*1 paddle 75 rpm

Refs. 1a and 1b were standard formulations, but formed a gel-like aggregate, and showed very poor disintegration and low dissolution rate. Ref. 1c in which a large amount of disintegrators was added also showed poor disintegration, and sufficient dissolution could not be obtained. Since AC220 has high solubility at low pH, a formulation with a pH adjustor was performed as Ref. 1d. The tablet of Ref. 1d showed good initial dissolution in dissolution test 1. In the tablet of Ref. 1e to which a forming agent was added, the disintegration was improved, but the initial dissolution was 72%, which was not sufficient. In dissolution test 2, all the tablets of Refs. 1c, 1d, and 1e showed dissolution rates lower than that of the preparation that is dissolved before use disclosed in WO 2010/132787 at all the measuring points (times).

Reference Example 2: Solubilization Formulations

A solid dispersion (1:3) of AC220 with polyvinylpyrrolidone (PVP) was prepared by spray-drying, and was used to prepare the tablets (45 mg tablets) with the formulations shown in Table 2. The results of dissolution test 1 are shown in Table 2.

Figure 2:
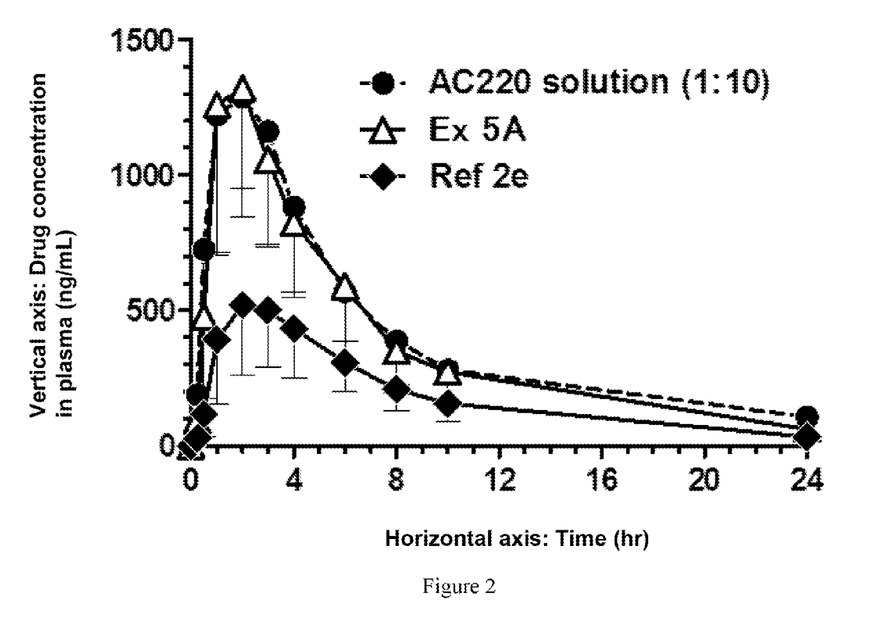
FIG. 2 is a graph showing the results of a dog BA test of the tablet of Ref. 2e in Reference Example 2, and the tablet of Ex. 5A in Example 5, along with the results of the preparation that is dissolved before use comprising the spray-dried material of AC220.2HCl and HPBCD at a 1:10 ratio by weight (administered in a liquid dosage form: AC220 solution (1:10)) disclosed in WO 2010/132787.

In dissolution test 1, the dissolution rate was improved by the addition of a pH adjustor (Ref. 2b). However, the disintegration and the dissolution tended to decrease by the addition of disintegrators (Refs. 2c and 2d). The tablet of Ref. 2e, which showed a good result in dissolution test 1, was used to perform the dog BA test. The results are shown in FIG. 2. The AUC from 0 to 24 hours of Ref. 2e was significantly poorer than that of the preparation that is dissolved before use comprising the spray-dried material of AC220.2HCl and HPBCD at a 1:10 ratio by weight (administered in a liquid dosage form: AC220 solution (1:10)) disclosed in WO 2010/132787. The results suggested that the bioavailability of the tablet could not be improved even if the solubility of AC220 was improved using its solid dispersion.

Reference Example 3: Tablets Using Composite and Commonly Used Formulations

AC220-HPBCD (1:10) which is a spray-dried powder of AC220.2HCl and HPBCD at a 1:10 ratio by weight obtained by a similar method as disclosed in Examples 6 to 8 of WO 2010/132787, was used to prepare the tablets (45 mg tablets)

TABLE 2

| Drug | Components (product name, code) | Ref 2a | Ref 2b | Ref 2c | Ref 2d | Ref 2e |
|---|---|---|---|---|---|---|
| Diluent | Granulated mannitol (Pearlitol 200SD) | — | 195.2 | 147.2 | — | 188.8 |
| Diluent | Crystalline cellulose (Ceolus PH-102) | 18.0 | — | — | 96.8 | — |
| Disintegrator | Croscarmellose sodium (Kicolate) | — | — | — | 48.0 | 24.0 |
| Disintegrator | Crospovidone | — | — | — | 48.0 | — |
| Disintegrator | L-HPC(LH-21) | — | — | 48.0 | — | — |
| pH Adjustor | Tartaric acid | — | 100.0 | 100.0 | 100.0 | 80.0 |
| Lubricant | Magnesium stearate | 2.0 | 4.8 | 4.8 | 7.2 | 7.2 |
| Tablet (mg) | | 200 | 480 | 480 | 480 | 480 |
| Preparation method | | DC | DC | DC | DC | DC |
| Tablet size | | 9 mm, round | 13.6 mm × 6.9 mm | 13.6 mm × 6.9 mm | 13.6 mm × 6.9 mm | 13.6 mm × 6.9 mm |
| Dissolution test 1 (D30 min) | | <10% | <70% | <30% | <20% | 86% | of the conventional formulations as shown in Table 3. As shown in Refs. 3c and 3e, the results of dissolution test 1 showed a trend toward improvement when the amounts of disintegrators were increased, but the disintegration of each tablet was not sufficient in any of the formulations, and a tablet exhibiting an initial release (D30 min>85%) could not be obtained.

TABLE 3

| Components (product name, code) | | Ref 3a | Ref 3b | Ref 3c | Ref 3d | Ref 3e |
|---|---|---|---|---|---|---|
| Drug | AC220-HPBCD (1:10) | 495.0 (61.9%) | 495.0 (61.9%) | 495.0 (58.9%) | 495.0 (86.8%) | 495.0 (66%) |
| Diluent | Crystalline cellulose (Ceolus UF-711) | 257.0 (32.1%) | 217.0 (27.1%) | — | — | — |
| Diluent | Crystalline cellulose (Ceolus PH-102) | — | — | — | 6.6 (1.2%) | 22.5 (3%) |
| Disintegrator | Sodium starch glycolate (Primojel) | 40.0 (5%) | — | — | — | — |
| Disintegrator | Croscarmellose sodium (Kicolate) | — | 40.0 (5%) | 168.0 (20%) | 28.5 (5%) | 150.0 (20%) |
| Disintegrator | Crospovidone | — | 40.0 (5%) | 84.0 (10%) | 28.5 (5%) | 75.0 (10%) |
| Disintegrator | L-HPC(LH-21) | — | — | 84 (10%) | — | — |
| Lubricant | Magnesium stearate | 8.0 (1%) | 8.0 (1%) | 9.0 (1.1%) | 11.4 (2%) | 7.5 (1%) |
| Tablet (mg) | | 800 | 800 | 840 | 570 | 750 |
| Preparation method | | DC | DC | Granul. (2 kN) | Granul. (2 kN) | Granul. (2 kN) |
| Tablet size | | 18.0 mm × 9.0 mm | 18.0 mm × 9.0 mm | 18.0 mm × 9.0 mm | 14.8 mm × 7.8 mm | 16.6 mm × 7.1 mm |
| Dissolution test 1 (D30 min) | | 40% | 60% | 80% | 40% | 80% |

To confirm the influence of HPBCD on preparations, HPBCD which did not contain AC220 was used to prepare the tablets (45 mg tablets) with the formulations shown in Table 4, and disintegration was observed. The results are shown in Table 4. It was confirmed that disintegration was decreased in accordance with an increase in the amount of HPBCD.

TABLE 4

| Components (product name, code) | | Ref 3f | Ref 3g | Ref 3h |
|---|---|---|---|---|
| | HPBCD | 450.0 | 180.0 | 0 |
| Diluent | Crystalline cellulose (Ceolus UF-711) | 262.0 (32.8%) | 532.0 (66.5%) | 712.0 (89%) |
| Disintegrator | Sodium starch glycolate (Primojel) | 40.0 (5%) | 40.0 (5%) | 40.0 (5%) |
| Disintegrator | Crospovidone | 40.0 (5%) | 40.0 (5%) | 84.0 (10%) |
| Lubricant | Magnesium stearate | 8.0 (1%) | 8.0 (1%) | 8.0 (1%) |
| | Tablet (mg) | 800 | 800 | 800 |
| | Preparation method | DC | DC | DC |
| | Tablet size | 18.0 mm × 9.0 mm | 18.0 mm × 9.0 mm | 18.0 mm × 9.0 mm |
| | Disintegration | Poor | Slightly poor | Good |

Example 1: Examination of Intermolecular Interaction of AC220

Figure 1:
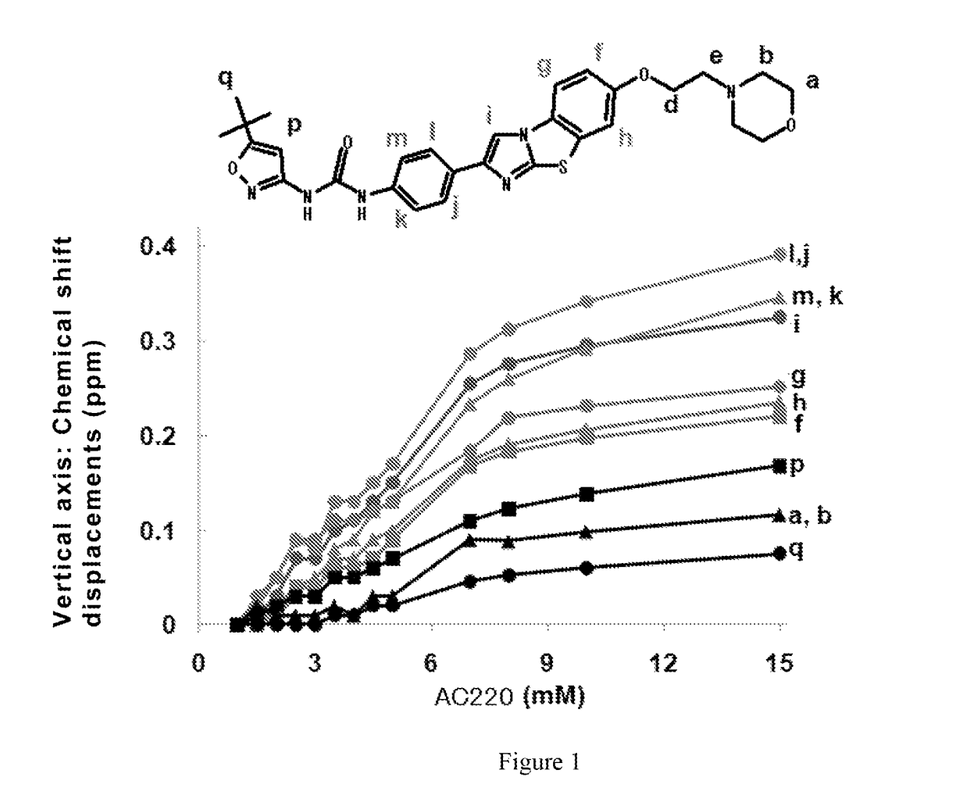
FIG. 1 is a graph showing the proton chemical shift displacements of AC220 as a function of the concentration of AC220 aqueous solutions, as measured in Example 1. The symbols "a" to "q" indicate each corresponding proton on the structural formula in the graph. The vertical axis shows the proton chemical shift displacements (ppm), and the horizontal axis indicates the concentration of AC220 (mM).

The molecular state of AC220 in the aqueous solution was examined. AC220 was soluble in water but a gelation of the aqueous solution of AC220 was observed with an increase in the concentration of AC220. $^1$H chemical shift displacements in this gelation were measured. The results are shown in FIG. 1. The protons of d and e could not be analyzed due to the overlapping with other proton signals. The $^1$H signals of around the central aromatic rings shifted upfield, which suggested that the aromatic rings were strongly involved in the gel formation.

Further, the interaction of protons between the AC220 molecules was studied by NOESY (nuclear Overhauser effect correlated spectroscopy), which is a two-dimensional NMR method to detect protons which are spatially adjacent to each other, and as a result, cross peaks were observed at the central aromatic rings, and it was confirmed that π-π stacking between the aromatic rings was involved in the gel formation.

Furthermore, the Hill coefficient was calculated from the analysis of the $^1$H chemical shift displacements: the value was greater than 1, and indicated a network formation. It was confirmed that the addition of methanol to the AC220 aqueous solution inhibited the gel formation, and that the network was formed by intermolecular hydrogen bonding.

As described above, it was confirmed that AC220 had intracellular interactions consisting of an aggregate formation via π-π stacking and a network formation by hydrogen bonding and which were involved in the gel formation of the aqueous solution of AC220.

On the other hand, WO 2010/132787 discloses that HPBCD was added to AC220 as an anti-gelling agent in a ratio (AC220:HPBCD) of 1:10 by weight, and the mixture was spray-dried to prepare a preparation that is dissolved before use, then the preparation was reconstituted by aqueous solution to obtain a liquid dosage form in which gelling was prevented (for example, paragraphs [0073] to [0075] and [0088], and Examples 6 to 8). The above finding suggested that the gelling in aqueous liquid dosage form was prevented as a result of suppression of the intermolecular interaction of AC220. That is to say, it is suggested that tablets which have suppressed intermolecular interaction of AC220 can be provided by using the composite of AC220 and HPBCD in a ratio of about 1:10 by weight.

Example 2

As shown in Table 5, AC220-HPBCD (1:10) and magnesium stearate as a lubricant were dry-granulated and compressed to tablets (45 mg tablets). The moldability of each tablet was good, for example, the average tablet hardness (over 10 tablets) was 159 N. The results of dissolution tests 1 and 2 are shown in Table 5.

It was confirmed that the tablet exhibited a dissolution rate equivalent to that of the preparation that is dissolved before use (administered in a liquid dosage form: AC220 solution (1:10)) disclosed in WO 2010/132787 in dissolution test 2.

Example 3: Examination of Amount of Lubricants

As shown in Table 5, AC220-HPBCD (1:10) and lubricants were compressed into tablets (45 mg tablets). The moldability of each tablet was good. The results of dissolution tests 1 are shown in Table 5. When magnesium stearate with a high hydrophobicity was used as a lubricant, it was confirmed that the initial dissolution was suppressed when 2% of magnesium stearate was added (Ex. 3C). In contrast, the initial dissolution was good in the tablet (Ex. 3D) to which 2% of Sodium stearyl fumarate with a slightly poor hydrophobicity was added, and thus, it was suggested that the dissolution from tablets comprising the composite could be controlled by controlling the amount of lubricants dependent on their hydrophobicity.

TABLE 5

| Components (product name, code) | | Ex 2 | Ex 3A | Ex 3B | Ex 3C | Ex 3D |
| --- | --- | --- | --- | --- | --- | --- |
| Drug | AC220-HPBCD (1:10) | 495.0 (99%) | 495.0 (99%) | 495.0 (98.5%) | 495.0 (98%) | 495.0 (98%) |
| Lubricant | Magnesium stearate | 5.0 (1%) | 5.0 (1%) | 7.6 (1.5%) | 10.1 (2%) | — |
| Lubricant | Sodium stearyl fumarate | — | — | — | — | 10.1 (2%) |
| Tablet (mg) | | 500 | 500 | 502.6 | 505.1 | 505.1 |
| Preparation method | | Granul. (2 kN) | DC | DC | DC | DC |
| Tablet size | | 14.8 mm × 7.8 mm | 14.8 mm × 7.8 mm | 14.8 mm × 7.8 mm | 14.8 mm × 7.8 mm | 14.8 mm × 7.8 mm |
| Dissolution test 1 (D30 min) | | 100% | 100% | 93% | 73% | 97% |
| Dissolution test 2 | | ○ | — | — | — | — |

TABLE 6

| Components (product name, code) | | Ex 4 |
| --- | --- | --- |
| Drug | AC220-HPBCD (1:10) | 495.0 (58.9%) |
| Diluent | Crystalline cellulose (Ceolus PH-102) | 36.6 (4.4%) |
| Foaming agent | Calcium carbonate | 200.0 (23.8%) |
| pH Adjustor | Tartaric acid | 100.0 (11.9%) |
| Lubricant | Magnesium stearate | 8.4 (1%) |
| Tablet (mg) | | 840 |
| Preparation method | | Granul. (5 kN) |
| Tablet size | | 16.6 mm × 7.1 mm |
| Dissolution test 1 (D30 min) | | 100% |
| Dissolution test 2 | | ○ |

Example 5

AC220-HPBCD (1:10) was used to prepare the tablets (45 mg tablets) with the formulations shown in Table 7. The moldability was good. The result of dissolution test 1 is Example 4

AC220-HPBCD (1:10) was used to prepare the effervescent tablets (45 mg tablets) with the formulation shown in Table 6. The moldability was good. The result of dissolution test 1 is shown in Table 6. The effervescent tablets were rapidly disintegrated, and the initial dissolution was good. Further, it was confirmed that the effervescent tablets exhibited a dissolution rate equivalent to that of the preparation that is dissolved before use (administered in a liquid dosage form: AC220 solution (1:10)) disclosed in WO 2010/132787 in dissolution test 2.

shown in Table 7. All the tablets were rapidly disintegrated, and the initial dissolution was good. Further, the tablets of Ex. 5A were used to perform the dog BA test (n=6). The results are shown in FIG. 2, along with the results of the preparation that is dissolved before use (administered in a liquid dosage form: AC220 solution (1:10)) disclosed in WO 2010/132787. The AUC from 0 to 24 hours of Ex. 5A was 0.96 times that of the AC220 solution (1:10), i.e., equivalent thereto. Further, it was confirmed that the dissolution of the tablets was not changed after the tablets had been stored in bottles with a desiccant or aluminum pouches under accelerated conditions (40° C./75RH %) for 6 months, and the tablets were extremely stable preparations in which the dissolution did not decrease after long-term storage.

TABLE 7

| Components (product name, code) | | Ex 5A | Ex 5B | Ex 5C |
|---|---|---|---|---|
| Drug | AC220-HPBCD (1:10) | 495.0 (91.7%) | 495.0 (91.7%) | 495.0 (91.7%) |
| Diluent | Crystalline cellulose (Ceolus PH-102) | 39.6 (7.3%) | — | — |
| Diluent | Granulated mannitol (Pearlitol 200SD) | — | 39.6 (7.3%) | 23.4 (4.3%) |
| Binder | Hydroxypropyl cellulose (HPC-SSL-SFG) | — | — | 16.2 (3%) |
| Lubricant | Magnesium stearate | 5.4 (1%) | 5.4 (1%) | 5.4 (1%) |
| | Tablet (mg) | 540 | 540 | 540 |
| | Preparation method | DC | DC | DC |
| | Tablet size | | 14.8 mm × 7.8 mm | |
| | Dissolution test 1 (D30 min) | 97% | 100% | 100% |

Example 6: Coated Tablets

The tablets of Ex. 5A obtained in Example 5 were coated with a film coating agent (product name: Opadry II 85F18422, Colorcon, USA; 15 mg/tablet) to obtain coated tablets having a tablet size of 15 mm×8 mm and a weight of 555.0 mg.

Example 7: Effect of Binders

The type and the amount of binders were varied as shown in Tables 8 and 9, and the tablets with the formulations shown in Tables 8 and 9 were prepared in a similar fashion to Example 5. The results of dissolution test 1 are shown in Table 8, along with the results of Ex. 5A described in Example 5. The initial dissolution tended to decrease when the amount of binders increased. It was confirmed that the criteria of high initial dissolution could be achieved by adding about 5% of a binder, sometimes depending on the type of binders.

TABLE 8

| Components (product name, code) | | Ex 5A | Ex 7A | Ex 7B | Ex 7C | Ex 7D |
|---|---|---|---|---|---|---|
| Drug | AC220-HPBCD (1:10) | 495.0 (91.7%) | 495.0 (88.9%) | 495.0 (87.0%) | 495.0 (88.9%) | 495.0 (87.0%) |
| Diluent | Crystalline cellulose (Ceolus PH-102) | 39.6 (7.3%) | 39.6 (7.1%) | 39.6 (7.0%) | 39.6 (7.1%) | 39.6 (7.0%) |
| Binder | Hydroxypropyl cellulose (HPC-SSL) | — | 16.7 (3.0%) | 28.4 (5.0%) | — | — |
| Binder | Hypromellose (TC-5R) | — | — | — | 16.7 (3.0%) | 28.4 (5.0%) |
| Lubricant | Magnesium stearate | 5.4 (1.0%) | 5.4 (1.0%) | 5.4 (1.0%) | 5.4 (1.0%) | 5.4 (1.0%) |
| Tablet (mg) | | 540 | 556.7 | 568.4 | 556.7 | 568.4 |
| Dissolution test 1 (D15 min) | | 73% | 70% | 65% | 65% | 66% |
| Dissolution test 1 (D30 min) | | 98% | 94% | 96% | 91% | 86% |

TABLE 9

| Components (product name, code) | | Ex 5A | Ex 7F | Ex 7G | Ex 7H | Ex 7J |
|---|---|---|---|---|---|---|
| Drug | AC220-HPBCD (1:10) | 495.0 (91.7%) | 495.0 (87.0%) | 495.0 (87.0%) | 495.0 (88.9%) | 495.0 (87.0%) |
| Diluent | Crystalline cellulose (Ceolus PH-102) | 39.6 (7.3%) | 39.6 (7.0%) | 39.6 (7.0%) | 39.6 (7.1%) | 39.6 (7.0%) |
| Binder | Hydroxypropyl cellulose (HPC-SL) | — | 16.7 (3.0%) | — | — | — |
| Binder | Hydroxypropyl cellulose (HPC-L) | — | — | 16.7 (3.0%) | — | — |
| Binder | Hypromellose (TC-5E) | — | — | — | 16.7 (3.0%) | — |
| Binder | PVP | — | — | — | — | 16.7 (3.0%) |
| Lubricant | Magnesium stearate | 5.4 (1.0%) | 5.4 (1.0%) | 5.4 (1.0%) | 5.4 (1.0%) | 5.4 (1.0%) |
| Tablet (mg) | | 540 | 556.7 | 556.7 | 556.7 | 556.7 |
| Dissolution test 1 (D15 min) | | 73% | 71% | 67% | 70% | 69% |
| Dissolution test 1 (D30 min) | | 98% | 90% | 90% | 95% | 92% |

Example 8: Effect of Disintegrators

The type and the amount of disintegrators were varied as shown in Tables 10 and 11, and the tablets with the formulations shown in Tables 10 and 11 were prepared in a similar fashion to Example 5. The results of dissolution test 1 are shown in Table 10, along with the results of Ex. 5A described in Example 5. The initial dissolution tended to decrease when the amount of a certain disintegrator increased. Sometimes depending the type of other excipients and disintegrators, it was confirmed that the initial dissolution did not remarkably decrease when about 10% of a disintegrator was added. However, when 10% of a disintegrator was added, the disintegration of tablets were not observed, and the dissolution profile showed a erosion pattern. These results suggested that it was difficult to improve the disintegration by the use of disintegrators in tablets of the AC220-HPBCD composite.

TABLE 10

| Components (product name, code) | | Ex 5A | Ex 8A | Ex 8B | Ex 8C | Ex 8D |
|---|---|---|---|---|---|---|
| Drug | AC220-HPBCD (1:10) | 495.0 (91.7%) | 495.0 (87.0%) | 495.0 (82.5%) | 495.0 (87.0%) | 495.0 (82.5%) |
| Diluent | Crystalline cellulose (Ceolus PH-102) | 39.6 (7.3%) | 39.6 (7.0%) | 39.6 (6.6%) | 39.6 (7.0%) | 39.6 (6.6%) |
| Disintegrator | Croscarmellose sodium (Kicolate) | — | 28.4 (5.0%) | 60.0 (10%) | — | — |
| Disintegrator | Sodium starch glycolate (Primojel) | — | — | — | 28.4 (5.0%) | 60.0 (10%) |
| Lubricant | Magnesium stearate | 5.4 (1.0%) | 5.4 (1.0%) | 5.4 (0.9%) | 5.4 (1.0%) | 5.4 (0.9%) |
| Tablet (mg) | | 540 | 568.4 | 600.0 | 568.4 | 600.0 |
| Dissolution test 1 (D15 min) | | 73% | 69% | 53% | 73% | 77% |
| Dissolution test 1 (D30 min) | | 98% | 95% | 84% | 94% | 97% |

TABLE 11

| Components (product name, code) | | Ex 5A | Ex 8E | Ex 8F | Ex 8G | Ex 8H |
|---|---|---|---|---|---|---|
| Drug | AC220-HPBCD (1:10) | 495.0 (91.7%) | 495.0 (87.0%) | 495.0 (82.5%) | 495.0 (87.0%) | 495.0 (82.5%) |
| Diluent | Crystalline cellulose (Ceolus PH-102) | 39.6 (7.3%) | 39.6 (7.0%) | 39.6 (6.6%) | 39.6 (7.0%) | 39.6 (6.6%) |
| Disintegrator | L-HPC(LH-21) | — | 28.4 (5.0%) | 60.0 (10%) | — | — |
| Disintegrator | Crospovidone | — | — | — | 28.4 (5.0%) | 60.0 (10%) |
| Lubricant | Magnesium stearate | 5.4 (1.0%) | 5.4 (1.0%) | 5.4 (0.9%) | 5.4 (1.0%) | 5.4 (0.9%) |
| Tablet (mg) | | 540 | 568.4 | 600.0 | 568.4 | 600.0 |
| Dissolution test 1 (D15 min) | | 73% | 66% | 61% | 72% | 75% |
| Dissolution test 1 (D30 min) | | 98% | 94% | 89% | 96% | 100% |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

The invention claimed is:

1. A tablet comprising, as an active ingredient, N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof, wherein N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof forms a composite with hydroxypropyl-β-cyclodextrin in a ratio ranging from 1:8 to 1:20 by weight, wherein the tablet comprises (1) the composite in an amount of about 85% by weight or more of the total weight of the tablet, (2) a lubricant selected from the group consisting of calcium stearate and magnesium stearate in an amount of about 0.5 to 1.5% by weight of the total weight of the tablet, or a lubricant selected from the group consisting of talc and sodium stearyl fumarate in an amount of about 0.5 to 2.5% by weight of the total weight of the tablet, (3) a diluent selected from the group consisting of microcrystalline cellulose and D-mannitol in an amount of about 3 to 10% by weight of the total weight of the tablet, and (4) hydroxypropyl cellulose in an amount of about 0 to 4% by weight of the total weight of the tablet.

2. The tablet of claim 1, wherein (2) magnesium stearate is in an amount of about 1% by weight of the total weight of the tablet, (3) a diluent is selected from the group consisting of microcrystalline cellulose and D-mannitol in an amount of about 4 to 7.5% by weight of the total weight of the tablet, and (4) hydroxypropyl cellulose is in an amount of about 0 to 4% by weight of the total weight of the tablet.

3. The tablet of claim 1, which is a tablet obtainable by forming a composition comprising the composite into a tablet.

4. The tablet of any one of claim 1, wherein the tablet is a coated tablet.

5. The tablet of claim 4, wherein the coated tablet is a film coated tablet.

6. The tablet of claim 1, wherein the composite is a composite of N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof and hydroxypropyl-β-cyclodextrin in a ratio of 1:10 by weight.

7. The tablet of claim 1, wherein the composite is spray-dried powder.

8. The tablet of claim 1, wherein the composite is lyophilized powder.

9. The tablet of claim 1, wherein N-(5-tert-butyl-isoxazol-3-yl)-N'-{4-[7-(2-morpholin-4-yl-ethoxy)imidazo[2,1-b][1,3]benzothiazol-2-yl]phenyl}urea or a pharmaceutically acceptable salt thereof is N-(5-tert-butyl-isoxazol-3-yl)-N'-{4-[7-(2-morpholin-4-yl-ethoxy)imidazo[2,1-b][1,3]benzothiazol-2-yl]phenyl}urea dihydrochloride.

* * * * *